United States Patent
Geneste et al.

(10) Patent No.: US 7,919,233 B2
(45) Date of Patent: Apr. 5, 2011

(54) MOTIF OF THE BECLIN PROTEIN WHICH INTERACTS WITH ANTI-APOPTOTIC MEMBERS OF THE BCL-2 PROTEIN FAMILY, AND USES

(75) Inventors: Olivier Geneste, Rueil-Malmaison (FR); John Hickman, Paris (FR); Jean-Christophe Rain, Ermont (FR)

(73) Assignee: Les Laboratoires Servier, Suresnes Cedex (FR)

( * ) Notice: Subject to any disclaimer, the term of this patent is extended or adjusted under 35 U.S.C. 154(b) by 400 days.

(21) Appl. No.: 11/883,438

(22) PCT Filed: Jan. 31, 2006

(86) PCT No.: PCT/FR2006/000205
§ 371 (c)(1),
(2), (4) Date: Jul. 31, 2007

(87) PCT Pub. No.: WO2006/082303
PCT Pub. Date: Aug. 10, 2006

(65) Prior Publication Data
US 2009/0099072 A1 Apr. 16, 2009

(30) Foreign Application Priority Data
Feb. 1, 2005 (FR) .................................... 05 00977

(51) Int. Cl.
*G01N 33/574* (2006.01)
*G01N 33/53* (2006.01)
(52) U.S. Cl. ............................................. 435/4; 435/7.1
(58) Field of Classification Search .................. None
See application file for complete search history.

(56) References Cited

U.S. PATENT DOCUMENTS 5,858,669 A * 1/1999 Levine ............................. 435/6
6,432,914 B1 * 8/2002 Levine ............................. 514/2

OTHER PUBLICATIONS

Pattingre et al Cell, vol. 122 p. 927-39, 2005.*
Willis et al , Current Opinion in Cell Bio. 17:617-625, 2005.*
Pisoni et al Farmaco,Nov.-Dec.;60(11-12):938-43. Epub Jul. 27, 2005.*
Oberstein et al JBC, 282: 13123-32, Apr. 2007.*
Sequence search result, 2009.*
Sequence search result-2, 2009.*
Bouillet et al , J Cell Sci. 115:1567-74, 2002.*
Xiao Huang Liang, et al., "Induction of autophagy and inhibition of tumorigenesis by beclin 1" Nature, MacMillan Journals Ltd., vol. 402, pp. 672-676, Dec. 9, 1999.
Qian J., et al., "Discovery fo novel inhibitors of Bcl-xL using multiple high-throughout screening platforms" Analytical Biochemistry, vol. 328, No. 2, p. 131-138, May 15, 2004.
Shimizu Shigeomi, et al., "Role for Bcl-2 family proteins in a non-apoptotic programmed cell death dependent ofn autophagy genes" Nature Cell Biology, vol. 6, No. 12, p. 1221-1228, Dec. 2004.
Saeki K., et al., "Bcl-2 down-regulation causes autophagy in a caspase-independent manner in human lukemic HL60 Cells" Cell Death and Differentiiation, vol. 7, No. 12, p. 1263-1269, Dec. 2000.
French Preliminary Search Report for FR0500977 of Sep. 16, 2005.
Ng, et al., The Significance of Autophagy in Cancer. 2005, 43:183-187.
Pattingre, et al, Bcl-2 Antiapoptotic Proteins Inhibit Beclin 1-Dependent Autophagy. Cell, 2005, 122:927-939.
Chan, et al., Clinical and Experimantal Pharmacology and Physiology, 2004, 31:119-128.
Kutzki, et al., Journal of the American Chemical Society, 2002, 124:11838-11839.

* cited by examiner

*Primary Examiner* — Larry R. Helms
*Assistant Examiner* — Lei Yaol
(74) *Attorney, Agent, or Firm* — Hueschen and Sage

(57) ABSTRACT

The invention relates to a method of identifying modulators of programmed cell death, comprising an interaction between a motif of Beclin protein and an anti-apoptotic member of the family of Bcl-2 proteins and the detection of said interaction be means of fluorescence polarization. The modulators identified on the basis of said method are administered to cancer patients in order to induce apoptotic- and/or autophagic-type programmed cell death. The invention also relates to a motif of the Beclin protein which can interact with an anti-apoptic member of the family of Bcl-2 proteins and to the use thereof in order to induce programmed cell death in a cancer patient.

5 Claims, 5 Drawing Sheets

Figure 3:
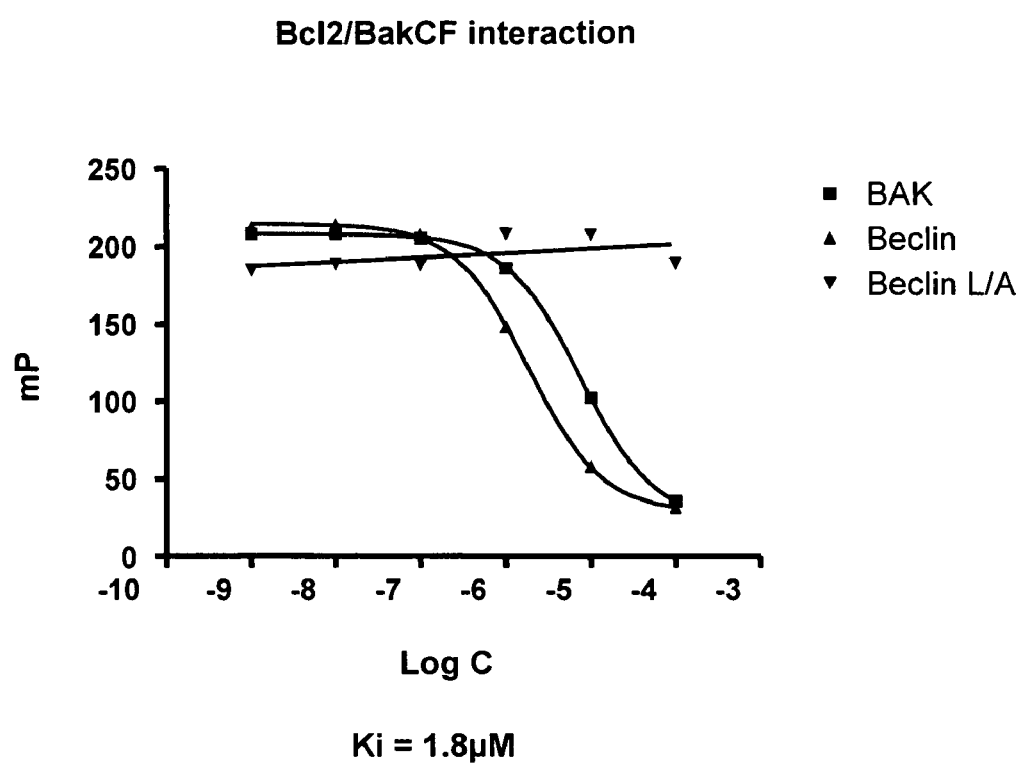

Figure 1: Amino acid sequence SEQ ID NO.1 of the motif of Beclin which interacts with an anti-apoptotic member of the Bcl-2 protein family Gly Thr Met Glu Asn Leu Ser Arg Arg Leu Lys Val Thr Gly Asp Leu Phe
G   T   M   E   N   L   S   R   R   L   K   V   T   G   D   L   F Asp Ile Met Ser Gly Gln Thr Asp Val
D   I   M   S   G   Q   T   D   V

Figure 2: Nucleic acid sequence SEQ ID NO.2 coding for the motif of Beclin which interacts with an anti-apoptotic member of the Bcl-2 protein family

GGCACCATGGAGAACCTCAGCCGAAGACTGAAGGTCACTGGGGACCTT
TTTGACATCATGTCGGGCCAGACAGATGTG

Figure 3 : Determination of Ki, using fluorescence polarisation, of the mutant or non-mutant Beclin competitor peptide with respect to the interaction between the pro-apoptotic Bak peptide and the anti-apoptotic members Bcl-2, Bcl-$X_L$ and Bcl-W.
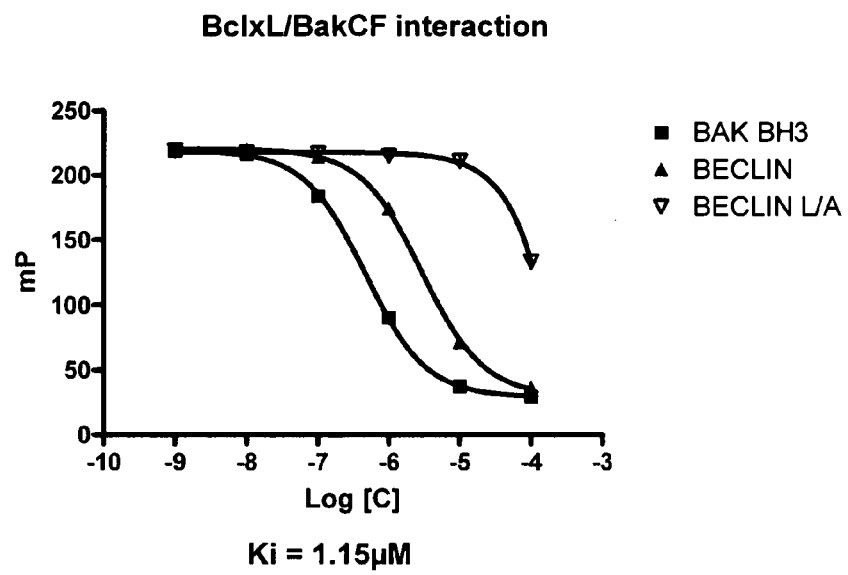
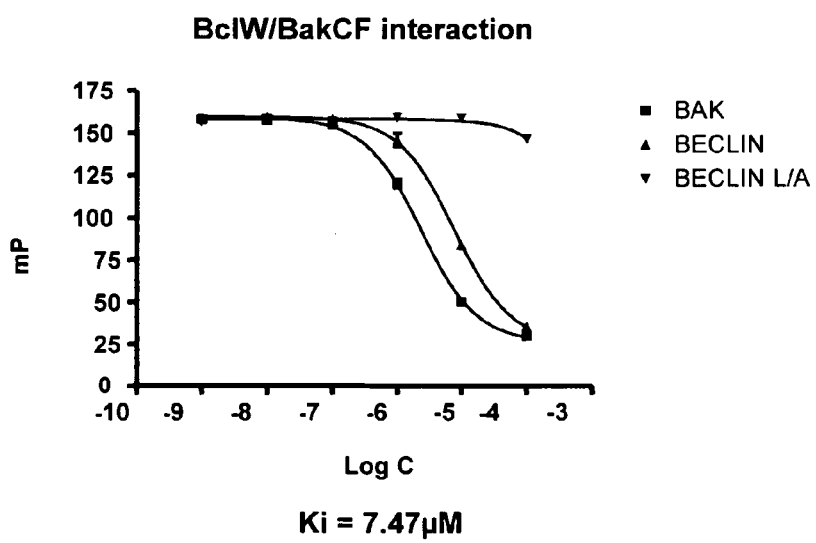

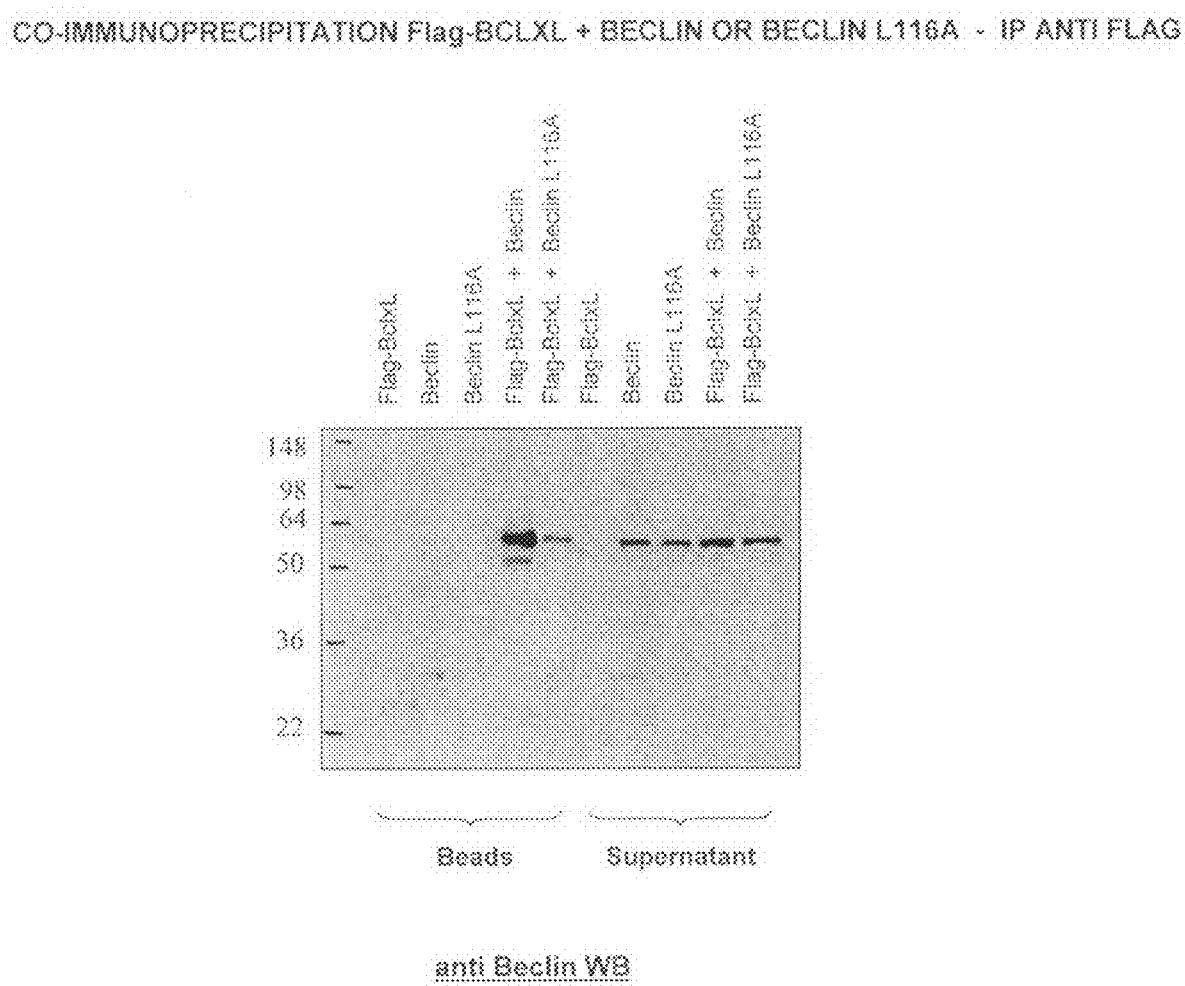
Figure 4 : Results of co-immunoprecipitation between the Bcl-X$_L$ protein and the Beclin protein.

Figure 5 : Determination of the $K_D$ of the interaction between Bcl-$X_L$ and the Beclin peptide
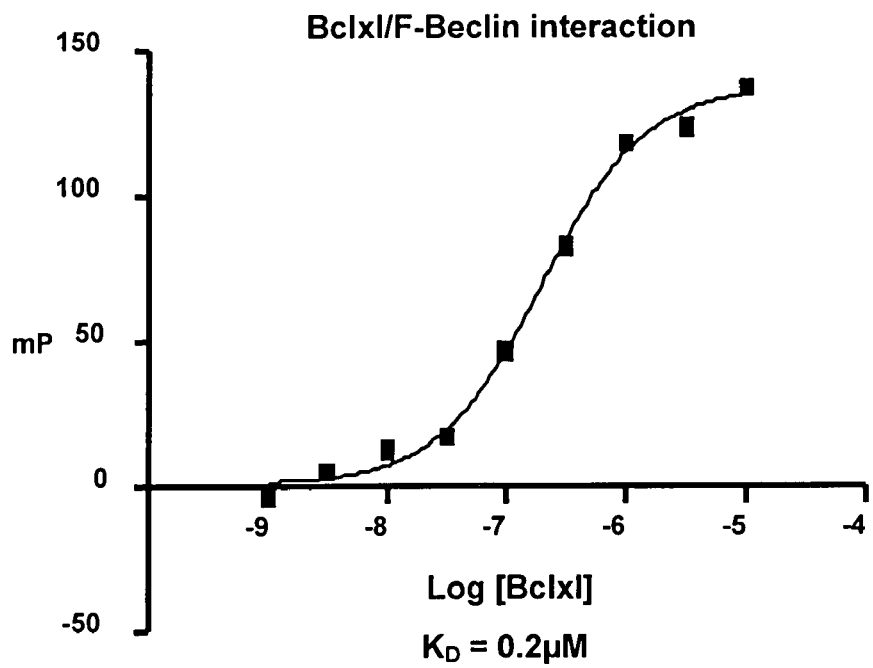
Figure 6 : Determination of the $IC_{50}$ of an antagonist of Bcl-$X_L$ (Ref 1)
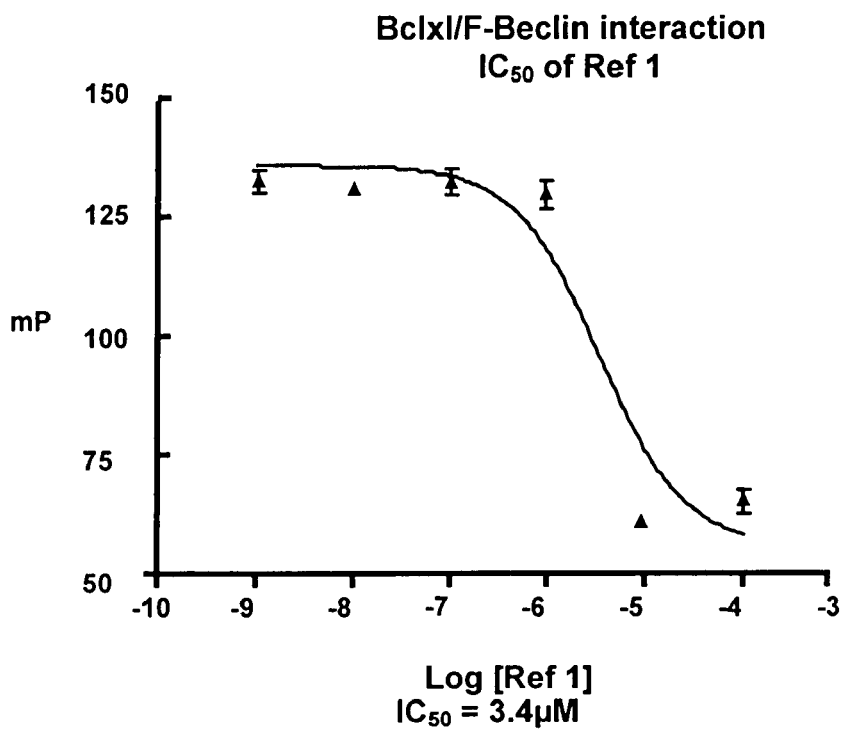

SEQUENCE LISTING

```
<160> NUMBER OF SEQ ID NOS: 5

<210> SEQ ID NO 1
<211> LENGTH: 26
<212> TYPE: PRT
<213> ORGANISM: Homo sapiens

<400> SEQUENCE: 1

Gly Thr Met Glu Asn Leu Ser Arg Arg Leu Lys Val Thr Gly Asp Leu
1               5                   10                  15

Phe Asp Ile Met Ser Gly Gln Thr Asp Val
            20                  25

<210> SEQ ID NO 2
<211> LENGTH: 78
<212> TYPE: DNA
<213> ORGANISM: Homo sapiens

<400> SEQUENCE: 2
ggcaccatgg agaacctcag ccgaagactg aaggtcactg gggaccttt tgacatcatg      60 tcgggccaga cagatgtg                                                   78

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gctttggaat cactacagg                                                  19

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
cacgatgcac gttgaagtg                                                  19

<210> SEQ ID NO 5
<211> LENGTH: 26
<212> TYPE: PRT
<213> ORGANISM: Artificial Sequence
```

-continued

```
<220> FEATURE:
<223> OTHER INFORMATION: Mutated Beclin Peptide

<400> SEQUENCE: 5

Gly Thr Met Glu Asn Leu Ser Arg Arg Ala Lys Val Thr Gly Asp Leu
1               5                   10                  15

Phe Asp Ile Met Ser Gly Gln Thr Asp Val
            20                  25
```

MOTIF OF THE BECLIN PROTEIN WHICH INTERACTS WITH ANTI-APOPTOTIC MEMBERS OF THE BCL-2 PROTEIN FAMILY, AND USES

The present invention lies within the field of seeking out and developing new agents which are useful in regulating apoptosis-type and/or autophagy-type programmed cell death in the treatment of patients with cancers.

The invention relates to a new method of identifying modulators of programmed cell death, comprising interaction between a motif of the Beclin protein and an anti-apoptotic member of the Bcl-2 protein family and detection of that interaction by fluorescence polarisation. The modulators identified by means of the method described above are administered to patients with cancers in order to bring about apoptotic-type and/or autophagic-type programmed cell death in those patients.

The invention relates in particular to a motif of the Beclin protein which is capable of interacting with an anti-apoptotic member of the Bcl-2 protein family and to the use thereof in bringing about programmed cell death in patients with cancers.

Programmed cell death is composed of, on the one hand, apoptosis and, on the other hand, autophagic death. Apoptosis is the better known phenomenon. This type of cell death involves morphological changes, such as nuclear condensation and DNA fragmentation, and also biochemical phenomena, such as activation of caspases which then degrade key structural components of the cell so as to bring about its disassembly and death. Regulation of the process of apoptosis is complex and involves the activation or repression of several intracellular signalling pathways.

Autophagic death is a second, less well-known mechanism of programmed cell death. On the cellular level, autophagy can be summarised by three stages: formation of an initial autophagic vacuole (the autophagosome) and maturation of the autophagosome into a degradative vacuole and then the fusion thereof with the lysosome. Autophagic death accordingly involves lysosomal degradation processes which are characterised by the accumulation of autophagic vacuoles and which are independent of a caspase-type regulation pathway.

Deregulation of the cellular equilibrium that exists between growth, survival and programmed cell death is at the origin of numerous pathologies, such as cancers.

In accordance with its usual meaning, "cancer" is defined within the context of the invention by two principal characteristics: cell growth and proliferation that are not regulated by external signals, and the ability to invade tissues and also, in some cases, the ability to form metastases by colonising distant sites.

These characteristics are the consequence of intrinsic properties of cancerous cells, that is to say their genomic and karyotypic instability, their uncontrolled proliferation and their metastatic ability, accompanied by the acquisition of new phenotypes and also by the activation and derepression of oncogenes in those cancerous cells. Within the context of the present invention, "cancer" is accordingly understood to be any phase of cell growth or proliferation having the above characteristics, especially advancing towards the development of primary tumours and/or metastatic tumours (secondary tumours).

Keeping a cell alive or programming its death necessitates regulation of a major signalling pathway involving, in particular, proteins of the Bcl-2 family. Proteins of the Bcl-2 family are divided into three main classes. The anti-apoptotic proteins, such as Bcl-2, Bcl-$X_L$ and Bcl-W, have a high degree of homology in their four BH domains. The pro-apoptotic proteins are divided into two categories: on the one hand, the multi-domain proteins such as BAX and BAK and, on the other hand, pro-apoptotic proteins such as BID, NOXA, PUMA, BIK, BIM and BAD which are characterised by the presence of a single homologous domain, the BH3 motif (Cory and Adams, *The Bcl-2 family: regulators of the cellular life-or-death switch* Nature reviews vol. 2 September 2002).

The BH3 motif is an amphiphilic α-helical region whose sequence homology in the Bcl-2 protein family is relatively low. Furthermore, the presence of the BH3 motif is required in a protein in order to allow interaction with anti-apoptotic members of the Bcl-2 protein family. In fact, the activity of an anti-apoptotic member of the Bcl-2 protein family is regulated by the product of pro-apoptotic genes of said family, the two proteins assembling into heterodimers. When in that state, the anti-apoptotic member of the Bcl-2 protein family is inactive and it accordingly no longer has its anti-apoptotic activity. In addition, the specific interaction of the BH3 motif with anti-apoptotic members of the Bcl-2 protein family can be modified by modulators so as to bring about apoptotic-type programmed cell death in specific manner.

It is moreover to be noted that the apoptotic signalling pathway can also be modulated by viral infection strategies. In fact, a large number of viral proteins interfere with the apoptotic pathway by means of structural homology, functional mimicry or at the level of the transduction of pro- and anti-apoptotic signals. Accordingly, certain viruses encode anti-apoptotic analogues of Bcl-2 which inhibit the mitochondrial pathway or caspase inhibitors which block the effector phase. Premature apoptosis of the infected cell represents a defence mechanism of the host which limits the abundance of viral particles; in contrast, delayed apoptosis of the host cell allows the virus to replicate and spread.

Autophagy is involved in the survival mechanism of the cell and is also associated with the progression of programmed cell death. Numerous studies have established that autophagy is under the control of products of tumour suppressor genes such as Beclin, PTEN and TSC1. Inactivation of those genes and reduction of the autophagic capacity are early events in tumour progression in patients with cancers. Beclin plays an early and central part in the phenomenon of autophagy, in particular in the formation of autophagic vacuoles, or autophagosomes (Edinger et al. *Defective autophagy leads to cancer*, Cancer Cell December 2003).

Resistance of tumours to chemotherapeutic agents constitutes a central problem in medical oncology. The appearance of acquired resistance is found, which makes itself manifest in tumours which, having initially responded to the chemotherapy, subsequently—in the more or less short term—develop resistance to the treatments. Such resistance present in the tumour cells is generally associated with inhibition of the caspase-dependent pathway or apoptotic pathway of programmed cell death, on which the principal current anticancer treatments (cytotoxic agents) act. In order to be more effective, anticancer treatments must accordingly propose an alternative and/or complementary strategy to the treatments that act on the apoptotic pathway of programmed cell death with a view to overcoming, at least in part, the disadvantages of known treatments acting exclusively on apoptosis. The invention accordingly proposes acting on the autophagic and/or apoptotic pathway by means of dual modulators.

Consequently, modulation of the caspase-independent or autophagic pathway as performed in the context of the invention puts forward an alternative to treatments which act specifically on the apoptotic pathway.

In view of, on the one hand, the role of anti-apoptotic members of the Bcl-2 protein family in the process of apoptosis and, on the other hand, the role of the Beclin protein in the phenomenon of autophagy, as well as the importance of acquired resistance in tumour development, the value will be understood of acting simultaneously on the autophagic and apoptotic pathways of programmed cell death in the context of anticancer treatments. Consequently, it is essential to be able to identify modulators capable of acting both on anti-apoptotic members of the Bcl-2 family and on the Beclin protein. In order to facilitate and accelerate screening of those dual modulators, the inventors have developed a strategy consisting, on the one hand, of establishing the structural interaction between anti-apoptotic members of the Bcl-2 protein family and the Beclin protein and, on the other hand, of seeking out modulators of that interaction which are inherently capable of acting both on anti-apoptotic members of the Bcl-2 protein family and on the Beclin protein. Consequently, the dual modulators selected in that manner should be ideal for obtaining candidate medicaments for combating pathologies that deregulate apoptotic-type and/or autophagic-type programmed cell death.

Selection and identification of modulators of the protein interaction between the Beclin protein, or a specific motif thereof, and an anti-apoptotic member of the Bcl-2 protein family were studied using the two-hybrid system. This two-hybrid system was initially described and developed by Fields et al. (U.S. Pat. Nos. 5,283,173; 5,468,614; 5,667,973).

The two-hybrid system consists, to start with, of a test in yeast between two recombined proteins. The first protein, known as the "bait", is a fusion protein containing a DNA binding domain (or BD) bound upstream of a protein A. The second protein is also a fusion protein, commonly known as the "prey", containing an activation domain (or AD) bound to a protein B. The binding and activation domains commonly used are those of Gal4 or *E. coli* Lex A. Proteins A and B are an anti-apoptotic member of the Bcl-2 protein family and a specific motif of Beclin, respectively. The association of proteins A and B by protein interaction allows the formation, by complementation, of a functional domain (BD-AD) capable of binding to the binding site (or BS) present upstream of a reporter gene and ensuring the transcription of said reporter gene.

However, this conventional two-hybrid method has its limitations. It is well known, for example, that such screening methods can result in false positives and/or false negatives, and biochemical confirmations of the results obtained are necessary. The false positives obtained by the two-hybrid system are especially frequent and are responsible for demonstrating functional rather than structural interactions.

A more effective technique allowing false positives and/or false negatives to be minimised is described in the International Patent Application WO 99/42612 or the patent U.S. Pat. No. 6,187,535 and uses recombinant haploid yeasts containing the "bait" and "prey" polypeptides. This system allows detection of a greater number of "preys" using a single "bait" in a more precise, more reproducible and more sensitive manner than the other conventional methods used in the field.

Using the two-hybrid system, the inventors have established the existence of a structural interaction between anti-apoptotic members of the Bcl-2 protein family and the Beclin protein. This protein interaction between those partners, which is similar to that which exists in the regulation of the apoptotic phenomenon between anti- and pro-apoptotic partners of the Bcl-2 protein family, is involved in the equilibrium of the process of programmed cell death.

An original motif of the Beclin protein has, in particular, been identified within the context of the invention. This motif of the Beclin protein is capable of interacting in highly specific manner with anti-apoptotic members of the Bcl-2 protein family with a view to its being used for selecting specific modulators of apoptosis and/or autophagy. This specificity of interaction is related to the sequence, the three-dimensional structure and/or the helicity of the original motif of the Beclin protein.

This original motif of the Beclin protein, having 26 amino acids, corresponds in fact to the precise domain of interaction with Bcl-2, Bcl-$X_L$ and/or Bcl-W and has the typical structural criteria allowing the formation of homo- or hetero-dimers.

The size of this motif makes it an ideal candidate for developing a test allowing highly efficient screening of compounds that are capable of modulating interactions between the Beclin peptide and an anti-apoptotic protein. Numerous tests are found in the literature for screening modulators of protein-protein interactions but they often have limitations with regard to their sensitivity and their high-throughput feasibility. The methods customarily employed necessitate the use of complex tools (fusion proteins, recombinant proteins etc.) which are not very compatible with high-throughput screening. Very frequently they generate a high level of background noise and are of low reliability from a quantitative point of view: they provide a reduced reading window that does not allow optimum screening of the compounds tested.

As an alternative to the methods already available, a highly efficient screening test based on fluorescence polarisation has been employed in the present invention (Owicki et al., Journal of Biomolecular Screening, 5, 2000, 297-306). This technique allows, for example, measurement of the interaction between a fluorophore-labelled ligand and a receptor. The principle consists of measuring an increase in the polarisation of fluorescence emitted by the ligand when bound to its receptor compared to that emitted by the free ligand. The fluorescence polarisation of the free ligand is dependent on its molecular weight and will be greater the higher the molecular weight. Accordingly, when this test is carried out using a ligand of high molecular weight, having a high level of intrinsic fluorescence polarisation, it will be difficult to reliably evaluate the difference in fluorescence polarisation between the free ligand and the bound ligand. Using a ligand of minimal molecular weight, on the other hand, will allow that difference to be accentuated and consequently allow the precision of the method to be increased. It will accordingly be possible to better evaluate the real activity of a compound and to carry out high-throughput screenings.

The peptide according to the invention, corresponding to the motif GTMENLSRRLKVTGDLFDIMSGQTDV (SEQ ID NO.1) of Beclin, can, advantageously, be used in the screening of compounds which modulate the protein interaction between the motif of Beclin and an anti-apoptotic member of the Bcl-2 protein family, either by activating or by inhibiting that interaction.

The invention relates to a method of identifying modulators of programmed cell death, comprising a step of interaction between the GTMENLSRRLKVTGDLFDIMSGQTDV (SEQ ID NO.1) motif of the Beclin protein and an anti-apoptotic member of the Bcl-2 protein family and then a step of detection of the interaction in the presence, or not, of the compound under test.

Advantageously, the method of identifying modulators of programmed cell death comprises the following steps:

a) Fluorescence probe labeling of the GTMENLSR-RLKVTGDLFDIMSGQTDV (SEQ ID NO.1) motif of the Beclin protein;
b) Addition of an anti-apoptotic member of the Bcl-2 protein family to said motif;
c) Incubation of the partners described in a) and b) in the presence, or not, of the compound under test;
d) measurement of the fluorescence polarization; and
e) comparison of the measurement with, and without, the compound under test.

A "modulator" is understood to be any compound capable of increasing, preventing or at least limiting a specific activity such as a protein-protein interaction, enzymatic activity or binding to cellular receptors. In accordance with the present invention, modulators are inhibitors or indeed activators of protein interaction between the partners Beclin and anti-apoptotic members of the Bcl-2 protein family.

The invention relates also to a method of identifying an inhibitor of the interaction between the motif of the Beclin protein and an anti-apoptotic member of the Bcl-2 protein family, which is capable of decreasing the fluorescence polarisation compared to a control consisting of this interaction in the absence of modulator.

The invention relates furthermore to a method of identifying an activator of the interaction between the motif of the Beclin protein and an anti-apoptotic member of the Bcl-2 protein family, which is capable of increasing the fluorescence polarisation compared to a control consisting of this interaction in the absence of modulator.

The fluorescent ligand, i.e. the fluorescent Beclin peptide, has, after binding with the anti-apoptotic partner of the Bcl-2 protein family, a rotational constant which is lower than the corresponding free ligand and, as a result, the fluorescence emitted by the bound ligand becomes polarised. Consequently, an increase in the polarisation of the fluorescence emitted by the bound ligand is observed, compared to the free ligand.

In a preferred embodiment, the fluorescence probe used in the method of screening according to the invention is Bodipy, Oregon Green or, preferably, fluorescein.

More particularly, the anti-apoptotic member of the Bcl-2 protein family involved as interaction partner in the process of screening and identification according to the invention can be the protein Bcl-2, Bcl-$X_L$ or Bcl-W.

Advantageously, the anti-apoptotic member of the Bcl-2 protein family is a fusion protein. A "fusion protein" is understood to refer to the fusion between a domain of the protein Bcl-2, Bcl-$X_L$ or Bcl-W and a domain of a protein such as GST (glutathione S-transferase).

The present invention relates to a motif of Beclin having the amino acid sequence GTMENLSRRLKVTGDLFDIMSGQTDV (SEQ ID NO.1) and functional variants thereof.

An "amino acid sequence" is to be understood as being a peptide sequence isolated from the natural context, especially sequences that have been isolated, chemically synthesised and/or purified and, possibly, modified by genetic engineering.

"Functional variants" are understood as being amino acid sequences of the motif of Beclin which comprise conservative substitutions or conservative point mutations and which have substantially the same properties as the motif encoded by the sequence SEQ ID NO.1 or, that is to say, the ability to interact with an anti-apoptotic member of the Bcl-2 protein family. Conservative substitutions or mutations of the amino acid sequence SEQ ID NO.1 are, for example, the following: glycine by alanine (G-A), valine by leucine (V-L), aspartic acid by glutamic acid (D-E), asparagine by glutamine (N-Q), leucine by isoleucine (L-I), arginine by lysine (R-K).

The inventors have observed that the motif of Beclin having the peptide sequence SEQ ID NO.1 interacts with an anti-apoptotic member of the Bcl-2 protein family, such as Bcl-2, Bcl-$X_L$ or Bcl-W.

The invention relates also to the nucleic acid sequence 5'ggcaccatggagaacctcagccgaa-gactgaaggtcactggggacctttttgacatcatgtcgggcc agacagatgtg 3' (SEQ ID NO.2) coding for the original motif of the Beclin protein. This nucleic acid sequence according to the invention can be obtained by means of the genetic code starting from the amino acid sequence of the motif of Beclin and its variants.

The "variants" of that nucleic acid sequence are especially:
sequences that are capable of hybridising under stringent conditions with the nucleic acid sequence SEQ ID NO.2 or a sequence complementary thereto and that encode a polypeptide having substantially the same properties as the motif of Beclin encoded by the sequence SEQ ID NO.1, or
sequences of a mammal species that are homologous to the sequence SEQ ID NO.2 isolated from humans.

"Stringent conditions" are understood to be conditions which allow specific hybridisation of two sequences of single-stranded DNA at about 65° C., for example in a solution of 6×SSC, 0.5% SDS, 5× Denhardt's solution and 100 μg of non-specific carrier DNA or any other solution of equivalent ionic strength, and after washing at 65° C., for example in a solution of at most 0.2×SSC and 0.1% SDS or any other solution of equivalent ionic strength. The parameters defining the stringency conditions depend on the temperature at which 50% of the paired strands separate (Tm). For sequences comprising more than 30 bases, Tm is defined by the relationship: Tm=81.5+0.41 (% G+C)+16.6 Log(concentration of cations)−0.63 (% formamide)−(600/number of bases). For sequences of less than 30 bases in length, Tm is defined by the relationship: Tm=4 (G+C)+2(A+T). The stringency conditions can accordingly be adapted by the person skilled in the art in dependence on the size of the sequence, the content of GC and any other parameter, especially in accordance with the protocols described in Sambrook et al., 2001 (Molecular Cloning: A laboratory Manual, 3rd Ed., Cold Spring Harbor, laboratory press, Cold Spring Harbor, N.Y.).

"Sequences of a mammal species that are homologous to the sequence SEQ ID NO.2" are understood to be a sequence of similar structure to the sequence SEQ ID NO.2 and encoding a polypeptide having substantially the same properties in non-human species of mammals, especially primates, the rat or the mouse. The percentage identity between two homologous sequences in the functional regions is generally greater than 80%, preferably greater than 90%.

The invention relates also to a recombinant vector containing a nucleic acid sequence as claimed according to the invention. A vector is to be understood as any type of vector allowing introduction of the nucleic acid sequence into a host cell and, optionally, expression—in the host cell—of the polypeptide encoded by the nucleic acid sequence.

Such a vector is, for example, a plasmid, a cosmid, a bacterial artificial chromosome or a bacteriophage, containing the sequences necessary for expression of the motif of the Beclin protein.

Preferably, the recombinant vector according to the invention contains the sequences necessary for expression—in the host cell—of the claimed motif of the Beclin protein. These sequences are especially promoter sequences of transcription and translation in the host cell and also terminator sequences. The recombinant vector can also contain sequences coding for secretion signals allowing release of the translated proteins into the extracellular environment.

The invention relates also to host cells transformed by a recombinant vector according to the invention. In a particular embodiment, those host cells are bacterial cells such as, for example, *Escherichia coli* and streptococci or eukaryotic cells such as yeast cells, filamentous fungi cells, insect cells and, preferably, mammalian cells.

Transformation of appropriate host cells by a recombinant vector containing the nucleic acid sequences according to the invention allows the claimed motif of the Beclin protein to be expressed. Afterwards, it is possible to purify the proteins expressed in those host cells, using various methods known to the person skilled in the art and abundantly described in the prior art. There may be mentioned, for example, purification by precipitation with ammonium sulfate, by size-exclusion chromatography and, preferably, by affinity chromatography.

The peptide having the amino acid sequence SEQ ID NO.1 can also be custom-synthesised chemically by Neosystem. Chemical synthesis of SEQ ID NO.1 and its functional variants is carried out by synthesis on a solid support using the Boc/benzyl strategy with the aid of an "Applied Biosystems 430A" peptide synthesiser. The synthesis is based on the assembly on resin of the desired sequence and then deprotection of the N-terminal and C-terminal amino functions. In the case of the Boc/benzyl strategy it is necessary to introduce the amino acid Boc-L-Lys(Fmoc)-OH during synthesis of the peptide. After the full sequence has been assembled, the amino function is deprotected and the peptide is cleaved from the resin in the presence of a strong acid.

The invention relates also to a pharmaceutical composition comprising, as active ingredient, a peptide corresponding to the motif SEQ ID NO.1 of Beclin in accordance with the invention, in combination with one more pharmaceutically acceptable excipients.

In the context of the invention, "excipients" of a pharmaceutical composition are understood to be any agent which ensures that the active ingredient is transported into the internal tracts of the patient being treated. An "active ingredient" is understood to be any substance which is responsible for the pharmacodynamic or therapeutic properties of the pharmaceutical composition.

Among non-toxic, pharmaceutically acceptable excipients there may be mentioned, by way of example and without implying any limitation, diluents, solvents, preservatives, wetting agents, emulsifiers, dispersants, binders, swelling agents, disintegrants, retardants, lubricants, absorbency agents, suspension agents, colourants or flavourings.

The present invention relates not only to the pharmaceutical composition considered as such and defined above but also to the use of that composition in a method of bringing about apoptotic-type and/or autophagic-type programmed cell death in accordance with the invention.

The present invention accordingly relates to a method of bringing about apoptotic-type programmed cell death, i.e. the caspase-dependent pathway of programmed cell death, and/or autophagic-type programmed cell death, i.e. the caspase-independent pathway of programmed cell death, comprising the administration to a patient, especially a patient with cancer, of an effective amount of pharmaceutical composition comprising a peptide of Beclin having the sequence SEQ ID NO.1.

The invention relates also to a pharmaceutical composition comprising at least one modulator, activator or inhibitor, identified using the method of identifying modulators in accordance with the invention, as active ingredient of said composition, in combination with one or more pharmaceutically acceptable excipients.

The invention relates also to a method of bringing about apoptotic-type (caspase-dependent) programmed cell death and/or autophagic-type (caspase-independent) programmed cell death by means of the administration of an effective amount of the above-defined composition to a patient with cancer.

The pharmaceutical compositions as described above are suitable for use in the treatment of cancers by action on apoptotic-type and/or autophagic-type programmed cell death.

The compositions according to the invention are in a form suitable for oral, parenteral, nasal, per- or trans-cutaneous, rectal, perlingual, ocular or respiratory administration, especially tablets, dragées, sublingual tablets, sachets, paquets, capsules, glossettes, lozenges, suppositories, creams, ointments, dermal gels and drinkable or injectable ampoules.

The present invention is illustrated, without being limited thereby, by the following Figures and Examples:

FIG. 1: amino acid sequence SEQ ID NO.1 of the motif of Beclin which interacts with an anti-apoptotic member of the Bcl-2 protein family.

FIG. 2: nucleic acid sequence SEQ ID NO.2 coding for the motif of Beclin which interacts with an anti-apoptotic member of the Bcl-2 protein family.

FIG. 3: determination of Ki, using fluorescence polarisation, of the mutant or non-mutant Beclin competitor peptide with respect to the interaction between the pro-apoptotic Bak peptide and the anti-apoptotic members Bcl-2, Bcl-$X_L$ and Bcl-W.

FIG. 4: results of co-immunoprecipitation between the Bcl-$X_L$ protein and the Beclin protein.

FIG. 5: determination of the $K_D$ of the interaction between Bcl-$X_L$ and the Beclin peptide.

FIG. 6: determination of the $IC_{50}$ of a reference Bcl-$X_L$ antagonist.

EXAMPLE 1

Identification, by the Two-hybrid System, of the Peptide Described in FIG. 1

Three banks of human cDNA (placenta, brain, cell line CEMC7) were screened by the two-hybrid technique (Fields et al.) in yeast using the conjugation protocol described by Legrain et al. in Nature Genetics, 1997, vol. 16, 277-282 (U.S. Pat. No. 6,187,535).

1) Preparation of the "Baits" and "Preys"

a) The "baits" used are:

the C-terminal truncate (1-209) of Bcl-$X_L$ (accession number Z23115) fused to the LexA DNA binding domain the C-terminal truncate (1-211) of Bcl-2 (accession number XM_008738) fused to the LexA DNA binding domain.

These baits are expressed in *Saccharomyces cerevisiae* yeasts, strain L40Δgal4 (MATa ade2, trp1-901, leu2-3, 112, lys2-801, his3Δ200, LYS2 (lexAop)$_4$-HIS3, ura3-52::URA3 (lexAop)$_8$-LacZ, GAL4::Kan$^R$), and precultured at 30° C. in a synthetic medium lacking tryptophan (DO-Trp) until an optical density DO$_{600nm}$ of between 0.1 and 0.5, inclusive, is obtained. Fifty ml of a dilution of that preculture (DO$_{600nm}$=0.006) are incubated at 30° C. overnight.

b) A collection of *Saccharomyces cerevisiae* yeasts, strain YHGX13 (MATα Gal4Δ Gal80Δ ade2-101::Kan$^R$, his3, leu2-3-112, trp1-901, ura3-52 URA3::UASGAL1-LacZ, Met), containing the plasmids expressing the cDNA banks, fused to the Gal4 transcription activation domain, is obtained by transformation following selection on a culture medium lacking leucine (DO-Leu). These yeasts are divided into aliquots and stored at −80° C.

2) Conjugation

Conjugation is carried out using a "bait"/"prey" ratio of 2.

An amount of yeast "bait" cells obtained in Step 1)a) corresponding to 50 units of $DO_{600nm}$ is mixed with the yeast "preys" obtained in Step 1)b). After centrifugation, the sediment is resuspended in a YPGlu medium, spread onto YPGlu culture plates and incubated for 4 hours 30 minutes at 30° C. Selection of the conjugated yeasts containing a "bait" and a "prey" capable of interacting with one another is carried out in a DO-Leu-Trp-His medium: the absence of leucine and tryptophan makes it possible to maintain a selection pressure allowing only those yeasts that contain the two types of plasmid ("baits"/"preys") to grow; the absence of histidine from the medium makes it possible to select the conjugated yeasts containing a "bait" plasmid and a "prey" plasmid capable of interacting with one another: this complementation makes it possible to activate the HIS3 gene as a reporter gene coding for an enzyme involved in the biosynthesis of histidine.

3) Identification of Positive Clones

The "prey" fragments of a colony of yeasts selected according to the conjugation method described in paragraph 2) are amplified by PCR starting from a crude lysate of that colony using specific primers of the "prey" vector:

```
ABS1 5'-GCTTTGGAATCACTACAGG-3'    (SEQ ID NO.3)

ABS2 5'-CACGATGCACGTTGAAGTG-3'.   (SEQ ID NO.4)
```

The PCR products are then sequenced and the sequences obtained are identified by comparison with databases.

4) Identification of the Peptide Described in FIG. 1

For each "bait" fragment tested, the two-hybrid system allows a plurality of "prey" fragments to be identified. This identification is carried out by comparison of sequences of the selected "preys" using a software program such as Blastwun, which is available from the University of Washington.

EXAMPLE 2

Validation of the Interaction Between the Peptide Described in Example 1 and Bcl-2, Bcl-$X_L$ and/or Bcl-W 1) Determination of Ki Using Fluorescence Polarisation (FIG. 3)

The determination of Ki using fluorescence polarisation consists of measuring the competitive effect of the Beclin peptide on the interaction between the pro-apoptotic Bak peptide and anti-apoptotic members of the Bcl-2 protein family such as Bcl-$X_L$, Bcl-2 or Bcl-W.

The following reagents are mixed together in the order stated:
  a) competitor peptide at a final concentration of from 1 nM to 100 µM;
  b) fluorescent peptide ligand (Bak BH3 carboxyfluorescein) at a final concentration of 15 nM;
  c) anti-apoptotic member of the Bcl-2 protein family at a final concentration of 100 nM for Bcl-$X_L$ and of 1 µM for Bcl-2 and Bcl-W.

These reagents are dissolved in the interaction buffer ($Na_2HPO_4$ 20 mM pH 7.4, EDTA 1 mM, NaCl 50 mM and pluronic acid F-68 0.05%).

The mixture is then incubated for 30 minutes at ambient temperature and the fluorescence polarisation is determined on a Fusion apparatus (Packard) (excitation at 485 nm and reading at 530 nm). The values are given in mP (unit of fluorescence polarisation).

These fluorescence polarisation analyses demonstrated the competitive effect of the Beclin peptide on the peptide interaction between Bak and Bcl-$X_L$, Bcl-2 or Bcl-W. The Ki values obtained in the course of these fluorescence polarisation tests are as follows:

| | |
|---|---|
| Bcl-$X_L$/Bak/Beclin | Ki = 1.15 µM |
| Bcl-2/Bak/Beclin | Ki = 1.8 µM |
| Bcl-W/ Bak/Beclin | Ki = 7.4 µM |

These analyses demonstrate the high affinity of the Beclin peptide with respect to anti-apoptotic members of the Bcl-2 protein family.

2) Determination of Ki, Using Fluorescence Polarisation, with Mutant Beclin Peptide (L116A)

The determination of Ki using fluorescence polarisation consists of measuring the competitive effect of the Beclin peptide that has been mutated from leucine to alanine at position 116 of the complete sequence of the Beclin protein (L116A) on the interaction between the pro-apoptotic BAK peptide and anti-apoptotic members of the Bcl-2 protein family such as Bcl-$X_L$, Bcl-2 or Bcl-W.

The sequence of the mutant peptide (L116A) is as follows:

```
GTMENLSRRAKVTGDLFDIMSGQTDV.    (SEQ ID NO.5)
```

The protocol for the determination of Ki using fluorescence polarisation is the same as the protocol described above.

Comparison of the results of the fluorescence polarisation analyses shows a loss of competitive effect with the mutant Beclin protein (L116A) relative to the Beclin peptide according to the invention in the peptide interaction between the pro-apoptotic Bak peptide and anti-apoptotic members of the Bcl-2 protein family such as Bcl-$X_L$, Bcl-2 or Bcl-W.

3) Co-immunoprecipitation (FIG. 4)

HeLa cells are co-transfected (Effectene kit, Qiagen) with an expression vector coding for the Bcl-$X_L$ protein carrying a flag epitope and an expression vector coding for the wild-type or mutant (L116A) Beclin protein. Twenty-four hours after transfection, the cells are taken up in lysis buffer (Hepes 10 mM pH 7.5, KCl 150 mM, $MgCl_2$ 5 mM, EDTA 1 mM, Triton 0.4%, antiproteases and antiphosphatases), incubated in ice and centrifuged at 10000 rpm.

The supernatant (cell lysate) is then incubated for 2 hours in the presence of agarose beads conjugated to anti-Flag antibodies (Flag M2 agarose, Sigma).

The agarose beads are then centrifuged and washed in the lysis buffer, then taken up in Laemmli buffer and analysed by Western blots with anti-Beclin antibodies.

Co-immunoprecipitation of the anti-apoptotic protein Bcl-$X_L$ with the entire Beclin protein by protein-protein interaction confirmed that there is indeed a structural interaction between the Bcl-$X_L$ protein and the Beclin protein.

EXAMPLE 3

Screening Test for Compounds Capable of Inhibiting the Interaction Between Bcl-2 and/or Bcl-$X_L$ and the Peptide Obtained in Example 1

1) Determination of the $K_D$ Between the Peptide Obtained in Example 1 and Bcl-$X_L$ (FIG. 5)

The peptide obtained in Example 1, in fluorescent form (coupled to fluorescein) and dissolved in a buffer containing $Na_2HPO_4$ 20 mM pH 7.4, EDTA 1 mM, NaCl 50 mM, pluronic acid F-68 0.05% at a concentration of 15 nM, is incubated in the presence of increasing concentrations of the fusion protein GFT-Bcl-$X_L$ ($10^{-9}$ to $10^{-5}$M) and the fluorescence polarisation is then measured using an En Vision apparatus (Packard Perkin-Elmer). It was possible to determine a $K_D$ of 0.2 µM for this interaction.

2) Identification of Inhibitors of the Bcl-$X_L$-Peptide Interaction

The compounds under test are distributed on 384-well plates (Corning Flat Bottom) at a final concentration of 10 µg/ml. One well is filled with an equivalent amount of buffer/solvent without a test compound, for use as the control. The peptide obtained in Example 1, labelled with fluorescein, is added to each well so as to obtain a final concentration ranging from 1 to 100 nM. The fusion protein GST-Bcl-$X_L$, or GST-Bcl-2, or also GST-Bcl-W, is then added so as to obtain a final concentration of from 0.1 to 1 µM in a buffer containing $Na_2HPO_4$ 20 mM pH 7.4, EDTA 1 mM, NaCl 50 mM and pluronic acid F-68 0.05%. The fluorescence polarisation is then measured by an En Vision apparatus (Packard Perkin-Elmer). A significant reduction in the fluorescence polarisation recorded in the test carried out with the test compound compared to that obtained without the test compound (control well) allows the conclusion that the compound has inhibitory activity. Conversely, a significant increase in the fluorescence polarisation in the test with the test compound compared to the control allows the conclusion that the compound has activator activity.

FIG. 6 shows the result obtained with a reference compound that is an antagonist of Bcl-$X_L$ (Ref 1): compound 4 of A. D. Hamilton et al., J. Am. Chem. Soc., 2002, 124, 11838-11839.

It was possible to determine an $IC_{50}$ of 3.4 µM for this compound.

The invention claimed is:

1. The method of identifying modulators of programmed cell death, comprising the following steps:
   a) fluorescence probe labelling of the peptide GTMENLSRRLKVTGDLFDIMSGQTDV (SEQ ID NO. 1) motif of the Beclin protein;
   b) addition of an anti-apoptotic member of the Bcl-2 protein family to the motif of the Beclin protein;
   c) incubation in the presence of a test compound;
   d) measurement of the fluorescence polarisation; and
   e) comparison of the measurement with, and without, the test compound.

2. The method of claim 1, wherein the modulator of programmed cell death is an inhibitor, which reduces the fluorescence polarisation.

3. The method of claim 1, wherein the modulator of programmed cell death is an activator, which increases the fluorescence polarisation.

4. The method of claim 1, wherein the fluorescence probe is fluorescein.

5. The method of claim 1, wherein the anti-apoptotic member of the Bcl-2 protein family is the protein Bcl-2, Bcl-$X_L$ or Bcl-W.

* * * * *